(12) United States Patent
Shimomura et al.

(10) Patent No.: US 12,171,915 B2
(45) Date of Patent: Dec. 24, 2024

(54) LIGHTING DEVICE WITH INACTIVATION FUNCTION

(71) Applicant: Ushio Denki Kabushiki Kaisha, Tokyo (JP)

(72) Inventors: Shinji Shimomura, Tokyo (JP); Akira Ishikura, Tokyo (JP)

(73) Assignee: Ushio Denki Kabushiki Kaisha, Tokyo (JP)

( * ) Notice: Subject to any disclaimer, the term of this patent is extended or adjusted under 35 U.S.C. 154(b) by 0 days.

(21) Appl. No.: 18/550,090

(22) PCT Filed: Feb. 17, 2022

(86) PCT No.: PCT/JP2022/006308
§ 371 (c)(1),
(2) Date: Sep. 11, 2023

(87) PCT Pub. No.: WO2022/190802
PCT Pub. Date: Sep. 15, 2022

(65) Prior Publication Data
US 2024/0148931 A1 May 9, 2024

(30) Foreign Application Priority Data

Mar. 12, 2021 (JP) .................. 2021-040153

(51) Int. Cl.
*A61L 9/20* (2006.01)
*F21K 9/233* (2016.01)
(Continued)

(52) U.S. Cl.
CPC ............ *A61L 9/20* (2013.01); *F21K 9/233* (2016.08); *F21K 9/238* (2016.08); *F21S 8/026* (2013.01);
(Continued)

(58) Field of Classification Search
CPC ........ A61L 9/20; A61L 2209/12; F21K 9/233; F21K 9/238; H05B 47/115; H05B 45/385;
(Continued)

(56) References Cited

U.S. PATENT DOCUMENTS 11,007,292 B1 * 5/2021 Grenon .................... A61L 2/24
2016/0000953 A1 1/2016 Bettles et al.
(Continued)

FOREIGN PATENT DOCUMENTS

JP S63-187221 U 11/1988
JP H04-270608 A 9/1992
(Continued)

OTHER PUBLICATIONS

International Search Report issued in PCT/JP2022/006308; mailed Mar. 22, 2022.
(Continued)

*Primary Examiner* — Bao Q Truong
(74) *Attorney, Agent, or Firm* — Studebaker & Brackett PC

(57) ABSTRACT

Provided is a lighting device with an inactivation function, the lighting device allowing the addition of an inactivation function while being equal to conventional lighting devices in device size. The lighting device with the inactivation function includes: a UVC light source to emit ultraviolet light having a peak wavelength in a wavelength range from 200 nm to 230 nm; an LED light source to emit visible light; a single unit of an AC/DC converter to convert an AC voltage derived from an external power source into a DC voltage and output the DC voltage; a UVC light source-specific circuit part to convert the DC voltage output from the AC/DC converter into a voltage for lighting the UVC light source; and an LED light source-specific circuit part to
(Continued)

convert the DC voltage output from the AC/DC converter into a current for lighting the LED light source.

16 Claims, 8 Drawing Sheets

(51) Int. Cl.
  *F21K 9/238* (2016.01)
  *F21S 8/02* (2006.01)
  *F21V 9/06* (2018.01)
  *F21V 33/00* (2006.01)
  *H05B 45/385* (2020.01)
  *H05B 47/115* (2020.01)
  *F21W 131/20* (2006.01)
  *F21Y 113/00* (2016.01)
  *F21Y 115/10* (2016.01)

(52) U.S. Cl.
  CPC ............ *F21V 9/06* (2013.01); *F21V 33/0068* (2013.01); *H05B 45/385* (2020.01); *H05B 47/115* (2020.01); *A61L 2209/12* (2013.01); *F21W 2131/20* (2013.01); *F21Y 2113/30* (2023.05); *F21Y 2115/10* (2016.08)

(58) Field of Classification Search
  CPC ........ F21S 8/026; F21V 9/06; F21V 33/0068; F21Y 2115/10; F21Y 2113/30; F21W 2131/20
  See application file for complete search history.

(56) References Cited

U.S. PATENT DOCUMENTS

| | | |
|---|---|---|
| 2020/0215214 A1 | 7/2020 | Rosen et al. |
| 2020/0330638 A1 | 10/2020 | Hsu-Luk et al. |

FOREIGN PATENT DOCUMENTS

| | | |
|---|---|---|
| JP | 2015-072739 A | 4/2015 |
| JP | 2015-174026 A | 10/2015 |
| JP | 2018-190604 A | 11/2018 |
| JP | 6692407 B2 | 5/2020 |
| WO | 2016/044759 A1 | 3/2016 |

OTHER PUBLICATIONS

Notification of Transmittal of Translation of the International Preliminary Report on Patentability and Translation of Written Opinion of the International Searching Authority; PCT/JP2022/006308; mailed on Sep. 21, 2023.

An Office Action; "Notice of Reasons for Refusal," mailed by the Japanese Patent Office on Mar. 15, 2024, which corresponds to Japanese Patent Application No. 2021-040153 and is related to U.S. Appl. No. 18/550,090; with English language translation.

The extended European search report issued by the European Patent Office on Aug. 21, 2024, which corresponds to European Patent Application No. 22766766.4-1201 and is related to U.S. Appl. No. 18/550,090.

* cited by examiner

13b

LIGHTING DEVICE WITH INACTIVATION FUNCTION

TECHNICAL FIELD

The present invention relates to a lighting device and particularly relates to a lighting device with a function for inactivating bacteria or viruses.

BACKGROUND ART

Conventionally, halogen lamps and discharge lamps have been used as a light source for illumination at places such as ordinary households, commodity stores, or restaurants. In recent years, light-emitting diodes (LEDs) have been becoming the mainstream. For instance, Patent Document 1 below discloses a structure of a spotlight-type lighting device with an LED light source.

LED light sources have been becoming used not only in spotlight-type lighting devices but also in so-called downlight-type lighting devices, in which part of the device is embedded in a ceiling top panel or the like.

PRIOR ART DOCUMENT

Patent Document 1: JP-B2-6692407
Patent Document 2: JP-U-S63-187221

SUMMARY OF THE INVENTION

Problems to be Solved by the Invention

In recent years, infections caused by bacteria or viruses, which may be hereinafter collectively referred to as "pathogens", have been an issue, and under such circumstances, people want to inactivate pathogens in a space in which a lighting device including an LED light source is installed.

A known method for inactivating pathogens present in a space involves irradiating the space with ultraviolet light. Patent Document 2, for example, proposes a lighting fixture with a built-in germicidal lamp for the purpose of putting the lighting fixture to use in a kitchen and other places where food is handled daily. In the lighting fixture, a germicidal lamp that emits ultraviolet light with a wavelength of 254 nm and a fluorescent lamp that emits light for illumination are built into a body of the lighting fixture that has a boxy shape.

However, ultraviolet light that exhibits high light intensity in a wavelength range from 240 nm to 300 nm, as in the germicidal lamp described in Patent Document 2 above, poses a risk of affecting the human body when irradiated on a human. The skin is divided into three parts from superficial to deep: the epidermis, the dermis, and the hypodermis deeper than the dermis, and the epidermis is further divided into four layers from superficial to deep: the stratum corneum, the stratum granulosum, the stratum spinosum, and the stratum basale. When a human body is irradiated with ultraviolet light that exhibits high light intensity in a wavelength range from 240 nm to 300 nm, which includes a wavelength of 254 nm, a characteristic of germicidal rays, the ultraviolet light passes through the stratum corneum, reaches the stratum granulosum or the stratum spinosum or, in some cases, reaches the stratum germinativum, and is absorbed by DNA of cells present in these layers. This, as a result, causes a risk of skin cancer.

In contrast to this, an excimer lamp in which a light-emitting gas containing KrCl or KrBr is sealed, for example, provides ultraviolet light that has a peak wavelength in the wavelength range from 200 nm to 230 nm, i.e., ultraviolet light that poses a low risk to the human body. Thus, it is conceivable that implementing a lighting device that incorporates such an excimer lamp and an LED light source for illumination makes it possible to inactivate pathogens in a space while illuminating the space.

However, light sources, such as excimer lamps, that emit ultraviolet light (hereinafter referred to as a "UVC light source") require high voltage when lighting. Hence, an inverter circuit is a requisite for such light sources, and the light sources require an alternating current/direct current (AC/DC) converter that generates a DC voltage from a commercial voltage to input the DC voltage to the inverter circuit. Thus, when both an LED light source for illumination and a UVC light source for inactivation are incorporated into a shared lighting device, the lighting device needs to incorporate a large number of lighting circuits. This may result in a larger-scale lighting device.

Meanwhile, the sizes and shapes of general lighting devices are broadly defined. Therefore, it is undesirable to increase the size of a lighting device because of the built-in UVC light source within the lighting device. In particular, this explanation is obvious when an existing lighting device is replaced with a lighting device with an inactivation function. In other words, it is preferable to implement the lighting device equipped with the inactivation function while making sure that the size and shape of the conventional lighting device remain almost unchanged.

A lamp acting as the UVC light source (the excimer lamp in the above example) has a shorter life than that of the LED light source for illumination. Thus, it is assumed that the UVC light source is replaced at shorter time intervals as compared to the LED light source. Since spotlight-type and downlight-type lighting devices are generally installed on ceilings and are used, there is a concern that the larger overall size of the lighting devices will make lamp replacement work more difficult.

Given the above challenge, it is an object of the present invention to provide a lighting device with an inactivation function, the lighting device allowing the addition of an inactivation function while being equal to conventional lighting devices in device size.

Means for Solving the Problems

A lighting device with an inactivation function, according to the present invention, includes:
- a UVC light source to emit ultraviolet light having a peak wavelength in a wavelength range from 200 nm to 230 nm;
- an LED light source to emit visible light;
- a single unit of an AC/DC converter connected to an external power source, the AC/DC converter being configured to convert an AC voltage derived from the external power source into a DC voltage and output the DC voltage;
- a UVC light source-specific circuit part to convert the DC voltage output from the AC/DC converter into a voltage for lighting the UVC light source and supply the voltage to the UVC light source; and
- an LED light source-specific circuit part to convert the DC voltage output from the AC/DC converter into a current for lighting the LED light source and supply the current to the LED light source.

Herein, "inactivation" refers to a concept that includes killing bacteria or viruses or making infectivity or toxicity lost, and "bacteria" refers to microorganisms such as germs or fungi (mold).

As described above in the "PROBLEMS TO BE SOLVED BY THE INVENTION" section, a lamp acting as the UVC light source requires high voltage when lighting, and thus an inverter circuit is a requisite for the lamp. The lamp requires an AC/DC converter that generates a DC voltage from an external power source voltage (commonly, a commercial voltage) to input the DC voltage to the inverter circuit in a direct current manner. The LED light source that emits visible light requires a DC current when lighting and thus requires an AC/DC converter to generate a DC current (a DC voltage) from a commercial voltage.

From the viewpoint of stably lighting the UVC light source, the inverter circuit of the UVC light source imposes a limit on the magnitude of the allowable input voltage. In other words, a conventional ultraviolet lighting device incorporating a UVC light source includes an AC/DC converter (referred to as a "UVC light source-specific AC/DC converter" herein for convenience) in which a circuit is designed to generate a DC voltage from a commercial power source to input the DC voltage to an inverter circuit.

Meanwhile, the LED light source usually has a plurality of LED elements built-in, and a necessary level of the DC voltage is determined by a number of the LED elements, i.e., an optical output. In other words, a conventional lighting device incorporating an LED light source includes an AC/DC converter (referred to as an "LED light source-specific AC/DC converter" herein for convenience) in which a circuit is designed to generate a DC voltage to supply current needed to cause the LED elements to emit light.

If a UVC light source and an LED light source are to be simply incorporated into a shared lighting device, the lighting device needs to incorporate a UVC light source-specific AC/DC converter and an LED light source-specific AC/DC converter in which circuits are properly designed for the respective light sources, since levels of DC voltages needed to light the respective light sources differ from each other. The AC/DC converter is a circuit that includes a large number of elements because the circuit requires a rectifier circuit and a transformer. Thus, when the AC/DC converters for each of the light sources are incorporated into the lighting device, the size of the circuits for lighting increases. As a result, it may be difficult to mount a UVC light source while maintaining the same size and shape as a lighting device consisting of a conventional LED light source.

In contrast to this, the lighting device with the inactivation function according to the above configuration includes the single unit of the AC/DC converter to generate a DC voltage from the external power source. At the UVC light source-specific circuit part, the DC voltage output from the AC/DC converter is converted to the voltage for lighting the UVC light source and the converted voltage is output, and at the LED light source-specific circuit part, the DC voltage is converted to the current for lighting the LED light source and the current is output. This allows a shared use of the AC/DC converter, which includes a large number of circuits. As a result, even the lighting device incorporating both the UVC light source and the LED light source can have the size of circuits for lighting equal to that of the conventional LED lighting device.

Ultraviolet light emitted from the lighting device with the inactivation function according to the present invention can provide sterilization and virus inactivation performance intrinsic to ultraviolet light without causing erythema or keratitis on the skin or eyes of a human or an animal. In particular, taking advantage of a characteristic of being able to be used in an environment where a human is present in contrast to conventional ultraviolet light sources such as low-pressure mercury lamps, the product can be installed in such an environment indoors or outdoors to irradiate the entire environment and provide virus inhibition and bacteria elimination in the air and on a surface of members installed in the environment. This accords with Goal 3 "Ensure healthy lives and promote well-being for all at all ages" included in the Sustainable Development Goals (SDGs) led by the United Nations, and will greatly contribute to the goal target 3.3 "By 2030, end the epidemics of AIDS, tuberculosis, malaria, and neglected tropical diseases and combat hepatitis, water-borne diseases, and other communicable diseases".

The LED light source may include an LED element group made up of a plurality of LED elements connected in series, either in a single row or in a plurality of rows connected in parallel with each other;
    a voltage applied between both ends of the LED element group may be lower than the DC voltage output from the AC/DC converter; and
    the LED light source-specific circuit part may include a resistance component.

To supply the LED elements included in the LED light source with a DC current for lightning necessary for light emission, a DC voltage based on the voltage applied between both the ends of the LED element group of the plurality of the series-connected LED elements needs to be applied to the LED light source. The voltage applied between both the ends depends on the number of elements connected in series in the LED element group. The number of elements is set by brightness and standards that consumers require for the LED light source, and it is essentially difficult for a manufacturer side to freely change the number of the devices lighting device by lighting device.

In other words, depending on the spec of the lighting device, there may be a case where the DC voltage to be input to the inverter to light the UVC light source is higher than the voltage applied between both the ends of the LED element group. In this case, when the DC voltage output from the AC/DC converter is supplied as-is to the LED light source, the current flowing to the LED elements is much higher than a rated current, creating a risk of damage to the LED light source.

In contrast to this, as in the above configuration, the LED light source-specific circuit part including a resistance component is interposed between the AC/DC converter and the LED light source, thereby reducing the amount of the current supplied to the LED light source. As a result, despite a shared use of the AC/DC converter, allows rated values (a rated voltage/a rated current) to be supplied to both the UVC light source and the LED light source. In this case, the LED light source-specific circuit part can be implemented by including the resistance component as a minimum additional element compared with conventional circuits for UVC light source lighting. In other words, the lighting device according to the above configuration provides a substantial reduction in device size compared with a case in which AC/DC converters for the respective light sources are included.

The LED light source may include an LED element group made up of a plurality of LED elements connected in series, either in a single row or in a plurality of rows connected in parallel with each other;

a voltage applied between both ends of the LED element group may be higher than the DC voltage output from the AC/DC converter; and the LED light source-specific circuit part may include a DC/DC converter to increase the DC voltage output from the AC/DC converter.

Depending on the product, there may be a case where the voltage applied between both the ends of the LED element group is lower than the DC voltage to be input to the inverter to light the UVC light source. In this case, when the DC voltage output from the AC/DC converter is supplied as-is to the LED light source, the current flowing to the LED elements is much lower than the rated current, creating a risk of decline in the maximum brightness of the LED light source. There may also be a case where the current flowing to the LED elements does not reach a threshold current in the first place and the LED elements do not emit light.

In contrast to this, as in the above configuration, the LED light source-specific circuit part including a DC/DC converter to increase the DC voltage output from the AC/DC converter is interposed between the AC/DC converter and the LED light source, thereby helping to increase the amount of the current supplied to the LED light source to a rated value. As a result, despite a shared use of the AC/DC converter, allows rated values (a rated voltage/a rated current) to be supplied to both the UVC light source and the LED light source. The LED light source-specific circuit part can be implemented by including the DC/DC converter compared with conventional circuits for UVC light source lighting. Unlike the AC/DC converter, the DC/DC converter does not require a rectifier circuit and a transformer, which are each made up of a large number of parts, and thus can be implemented with an extremely simple circuit. In other words, the lighting device according to the above configuration provides a substantial reduction in device size compared with a case in which AC/DC converters for the respective light sources are included.

The LED light source-specific circuit part may include a resistance component disposed at a place between an output side terminal of the DC/DC converter and the LED light source.

Even in a case where the output voltage of the DC/DC converter and the voltage applied between both the ends of the LED element group diverge from each other, the above configuration allows the two voltage values to come closer to each other.

The lighting device with the inactivation function may include a housing that accommodates the UVC light source and the LED light source.

This allows a lighting device equipped with an inactivation function to be implemented by a single unit of the lighting device. In this case, it is preferred that the UVC light source-specific circuit part and the LED light source-specific circuit part are mounted on a shared substrate from the viewpoint of further decrease in device size.

The LED light source-specific circuit part may include a controller to provide a light modulation function for the LED light source.

The housing may have a shared light extraction surface through which both the ultraviolet light emitted from the UVC light source and the visible light emitted from the LED light source are extracted outside, and the housing may form a shape of a spotlight or a downlight.

This configuration allows the lighting device that is substantially similar to the conventional lighting device in external appearance to irradiate a space subject to lighting with visible light to light the space and irradiate the same space with ultraviolet light to inactivate pathogens.

The UVC light source may include a filter member to suppress light intensity of a component of the ultraviolet light belonging to a wavelength range of more than 240 nm.

If a KrCl excimer lamp or a KrBr excimer lamp, for example, is used as the UVC light source, ultraviolet light emitted from the light source hardly displays light intensity in a wavelength range of more than 240 nm. However, this ultraviolet light may exhibit light intensity in a wavelength range of more than 240 nm, albeit at a very low ratio (less than 10%) to the light intensity at the peak wavelength. The UVC light source as in the above configuration includes the filter member and thus, out of radiated ultraviolet light, light intensity in a wavelength range of more than 240 nm is further suppressed. This helps to further lessen the effect on the human body.

The filter member that may be used is, for example, a wavelength selection filter that transmits ultraviolet light in a wavelength range from 200 nm to 230 nm and blocks ultraviolet light in a wavelength range from 240 nm to 280 nm. As the wavelength selection filter, a dielectric multilayer film filter including a $HfO_2$ layer and a $SiO_2$ layer arranged in a stack is used, for example.

Effect of the Invention

According to the present invention, a lighting device equipped with an inactivation function can be implemented while the lighting device is equal to conventional lighting devices in device size.

MODE FOR CARRYING OUT THE INVENTION

Figure 1:
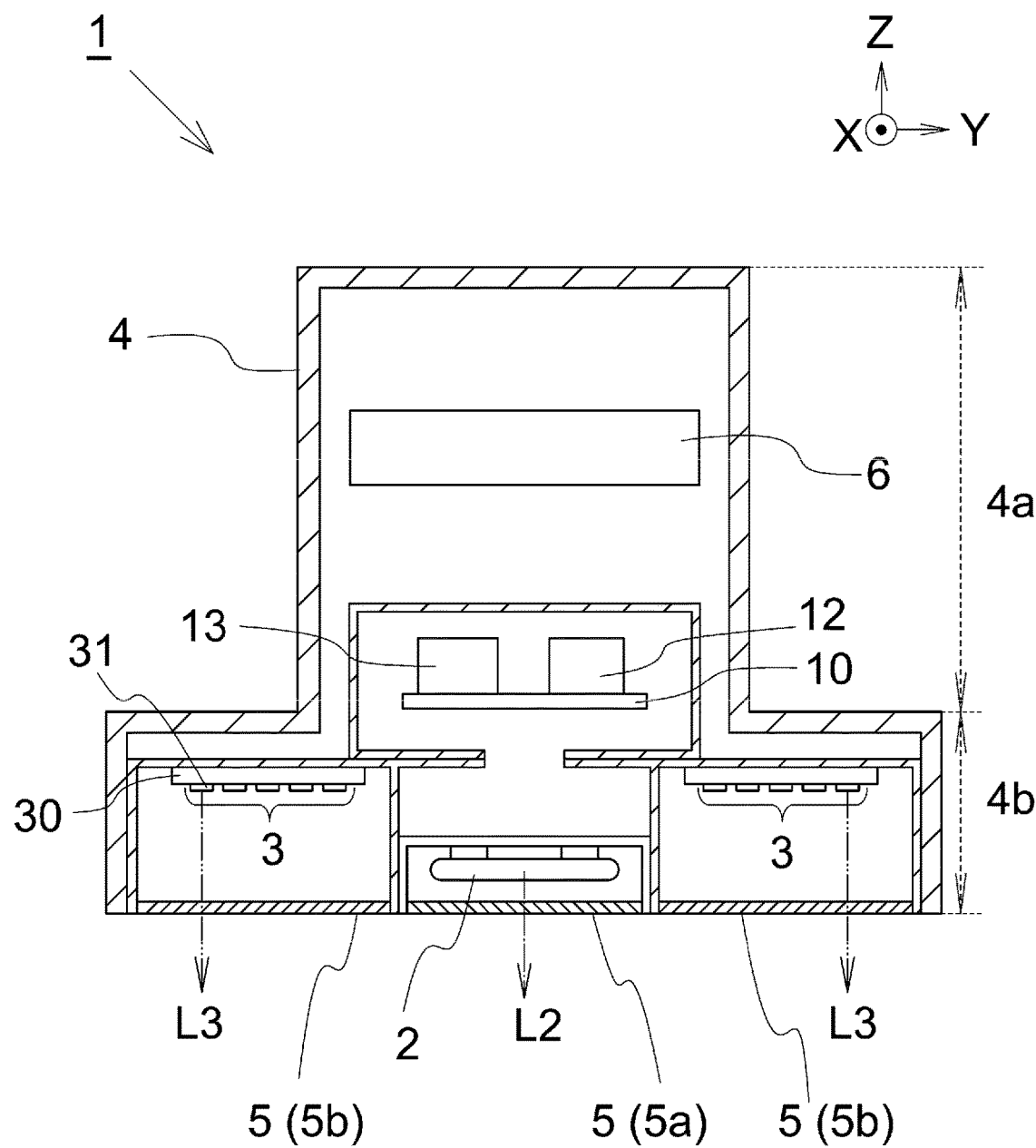
FIG. 1 is a schematic cross-sectional view illustrating a configuration of an embodiment of a lighting device with an inactivation function of the present invention.

An embodiment of a lighting device with an inactivation function according to the present invention will be described below with reference to the drawings. The drawings referred to below are schematic illustrations and the dimensional ratios in the drawings are not necessarily the same as the actual dimensional ratios. Furthermore, the dimensional ratios may not always be the same between the drawings.

In the following description, the lighting device with the inactivation function may simply be referred to as a "lighting device".

FIG. 1 is a schematic cross-sectional view of the lighting device of the present embodiment. It is assumed that a lighting device 1 shown in FIG. 1 is a downlight-type lighting device mounted on a ceiling.

Figure 2:
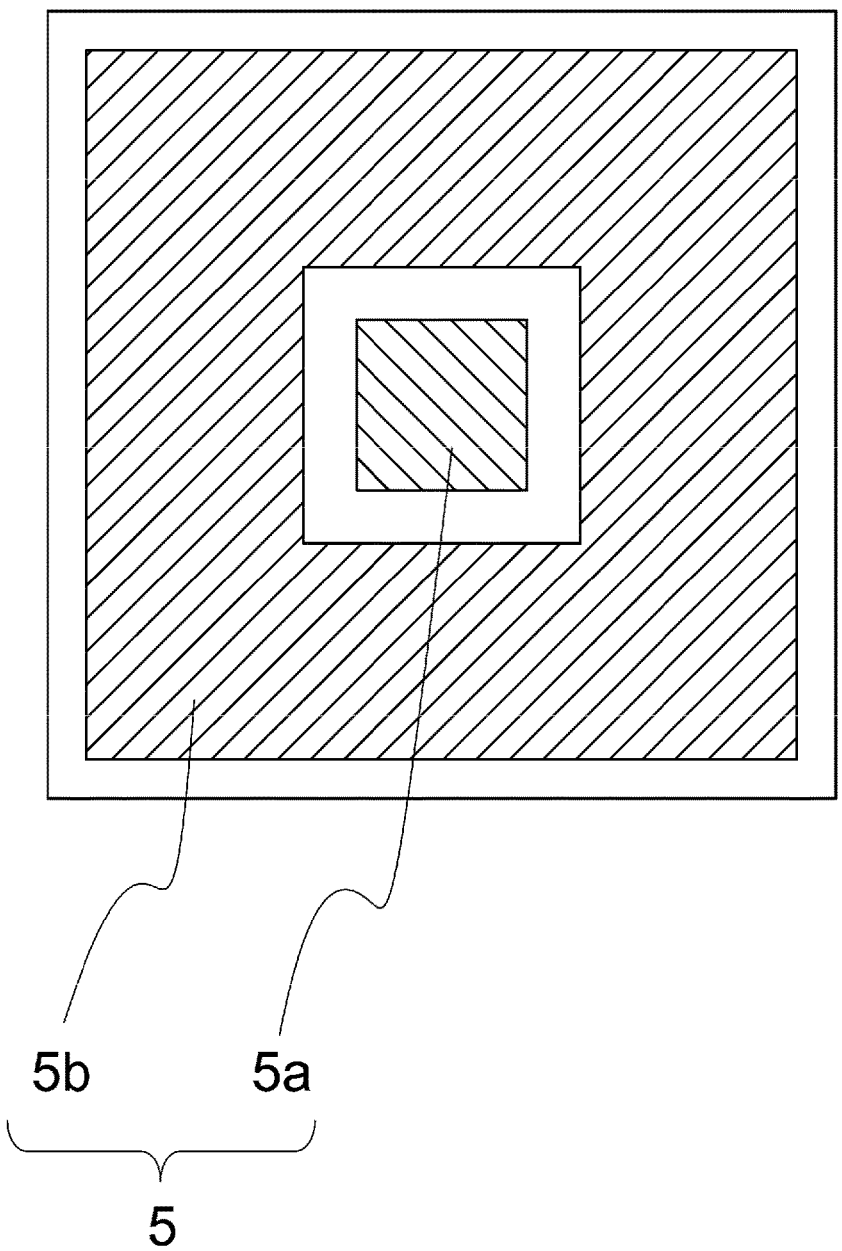
FIG. 2 is a schematic plan view of a light extraction surface included in the lighting device with the inactivation function in FIG. 1, viewed in a +Z direction.

The lighting device 1 includes a housing 4 and accommodates a UVC light source 2 to emit ultraviolet light L2 and an LED light source 3 to emit visible light L3 inside the housing 4. In FIG. 1, it is assumed that the lighting device 1 is installed on a ceiling (not shown) located on a +Z side relative to the lighting device 1 to emit the light (L2, L3) toward a −Z direction. In the following description, as shown in FIG. 1 and FIG. 2 described later, reference is made as appropriate to an X-Y-Z coordinate system in which a plane orthogonal to a Z direction is an XY plane.

In the present specification, when a distinction is made between a positive direction and a negative direction to express a direction, a positive or negative sign is given like a "+Z direction" or a "−Z direction", and when no distinction is made between positive and negative directions, the direction is simply written as a "Z direction" by omitting positive and negative signs. Namely, in the present specification, in the case where the direction is simply written as the "Z direction", both the "+Z direction" and the "−Z direction" are included. The same applies to the X direction and the Y direction.

In the housing 4, circuits (6, 12, 13) are accommodated in an upper region 4a located on the +Z side to light the light sources (2, 3), and the light sources (2, 3) are accommodated in a lower region 4b located on a −Z side. The regions (4a, 4b) of the housing 4 are cylindrical in shape and are coaxially arranged, for example. An example of the dimensions of the housing 4 is that the upper region 4a is 200 mm square in outer diameter and 100 mm high, and the lower region 4b is 400 mm square in outer diameter and 50 mm high.

In the upper region 4a of the housing 4, an AC/DC converter 6, a UVC light source-specific circuit part 12, and an LED light source-specific circuit part 13 are accommodated. The AC/DC converter 6 is a circuit designed to convert a commercial AC voltage (e.g., AC200V, AC100V) into a DC voltage. The UVC light source-specific circuit part 12 is a circuit designed to convert the DC voltage generated by the AC/DC converter 6 into a voltage for lighting the UVC light source 2 (a voltage V2 in FIG. 5 described later). The LED light source-specific circuit part 13 is a circuit designed to convert the DC voltage generated by the AC/DC converter 6 into a current for lighting the LED light source 3 (a current I3 in FIG. 5 described later). In the present embodiment, as shown in FIG. 1, the UVC light source-specific circuit part 12 and the LED light source-specific circuit part 13 are mounted on a shared substrate 10, and this is an example. The AC/DC converter 6 may also be mounted on the substrate 10. All the AC/DC converter 6, the UVC light source-specific circuit part 12, and the LED light source-specific circuit part 13 are mounted on the shared substrate 10, and the lighting device 1 further decreases in size. The AC/DC converter 6, the UVC light source-specific circuit part 12, and the LED light source-specific circuit part 13 are described in detail later.

In the lower region 4b of the housing 4, the UVC light source 2, the LED light source 3, and a light extraction surface 5 through which the light (L2, L3) emitted from the light sources (2, 3) is extracted outside of the lighting device 1 are disposed.

As shown in FIG. 1, the lighting device 1 of the present embodiment has the light extraction surface 5 at a place on the −Z side of the housing 4. The light extraction surface 5 includes an area 5a to extract the ultraviolet light L2 emitted from the UVC light source 2 and an area 5b to extract the visible light L3 emitted from the LED light source 3. FIG. 2 is a schematic plan view of the light extraction surface 5, viewed in the +Z direction. The light extraction surface 5 included in the lighting device 1 of the present embodiment includes the area 5b, through which the visible light L3 is extracted, outside the area 5a, through which the ultraviolet light L2 is extracted. As a result, a light distribution angle of the visible light L3 is widened, and this makes it possible to implement inactivation inside a target space while lighting the target space with increased efficiency.

However, in the present invention, a form of the light extraction surface 5 included in the lighting device 1 is not limited. In other words, in FIG. 2, a positional relationship between the area 5a through which the ultraviolet light L2 is extracted and the area 5b through which the visible light L3 is extracted may be changed inversely. The area 5a and the area 5b may be disposed adjacent to each other in the X direction or the Y direction. Further, the area 5a and the area 5b may be disposed on different surfaces. More specifically, the lighting device 1 may include a light extraction surface 5a for the ultraviolet light L2 and a light extraction surface 5b for the visible light L3, and the light extraction surfaces (5a, 5b) may be disposed at respective different places of the housing 4.

Preferably, a diffusion member is disposed especially on the area 5b of the light extraction surface 5 to diffuse the visible light L3 and irradiate the target space with the diffused light.

Figure 3:
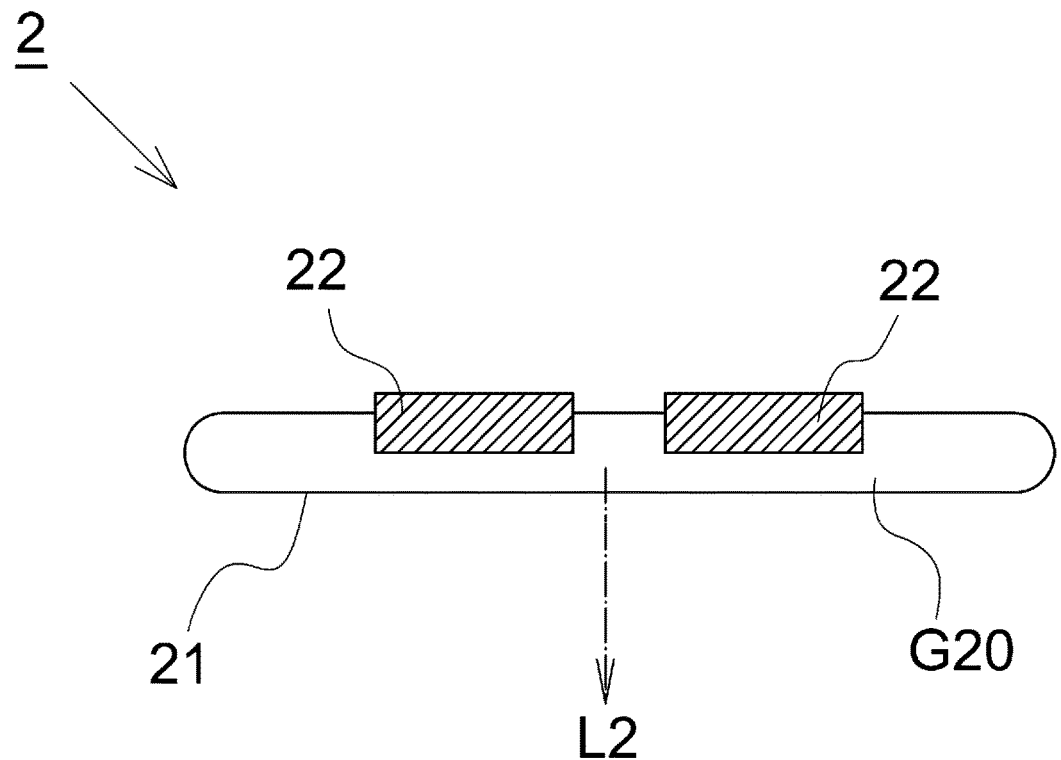
FIG. 3 is a schematic side view illustrating a structure of an excimer lamp as an example of a UVC light source.

In the present embodiment, the UVC light source 2 is made up of an excimer lamp. More specifically, as shown schematically in FIG. 3, the UVC light source 2 includes a light-emitting tube 21 and a pair of electrodes (22, 22). FIG. 3 is a schematic side view of the UVC light source 2 made up of an excimer lamp.

In the UVC light source 2 shown in FIG. 3, the pair of electrodes (22,22) are arranged so as to be in contact with an outer surface of the light-emitting tube 21 of the excimer lamp. The pair of electrodes (22,22) are arranged at places separated from each other in a tube-axis direction of the light-emitting tube 21. The pair of electrodes (22,22) are made of a conductive material, preferably a material exhibiting reflectivity to the ultraviolet light L2 emitted from the light-emitting tube 21. In one example, the pair of electrodes (22,22) are both made of Al, an Al alloy, stainless steel, or the like.

A light-emitting gas G20 is sealed in the light-emitting tube 21 of the excimer lamp. When a high-frequency AC voltage of, for example, about several kHz to 5 MHz is applied between the pair of electrodes (22,22) from the UVC light source-specific circuit part 12, the voltage is applied to the light-emitting gas G20 via the light-emitting tube 21 of the excimer lamp. At this time, discharge plasma is generated in a discharge space in which the light-emitting gas G20 is sealed, so that atoms of the light-emitting gas G20 are excited to be brought into an excimer state, and excimer light emission occurs when the atoms shift to the ground state.

The light-emitting gas G20 is made of a material that emits the ultraviolet light L2 having a peak wavelength in a wavelength range from 200 nm to 230 nm at the time of excimer emission. In one example, the light-emitting gas G20 contains KrCl or KrBr.

For example, when the light-emitting gas G20 contains KrCl, the light-emitting tube 21 of the excimer lamp emits the ultraviolet light L2 having a peak wavelength of around 222 nm. When the light-emitting gas G20 contains KrBr, the light-emitting tube 21 of the excimer lamp emits the ultraviolet light L2 having a peak wavelength of around 207 nm. The peak wavelength for the KrCl excimer lamp is described as "around 222 nm", which is intended to include a difference among individual excimer lamp products and permit not only absolutely precise 222.0 nm but also a wavelength error of ±3.0 nm inclusive from the reference point, 222.0 nm. Similar considerations apply to the KrBr excimer lamp.

A fluorescent material (not shown) may be disposed on a tube wall of the light-emitting tube 21. In this case, the peak wavelength of ultraviolet light emitted from the light-emitting gas G20, which is sealed in the light-emitting tube 21 of the UVC light source 2, at the time of excimer emission may be less than 200 nm. The fluorescent material may be a material that converts incident excimer light into light (ultraviolet light) having a peak wavelength in a wavelength range from 200 nm to 230 nm. A material gas that can be used as the light-emitting gas G20 is Xe or ArF, for example, which emits excimer light having a peak wavelength of less than 200 nm. In this case, a material that can be used as the fluorescent material is $LaPO_4$:Pr, $K_2YF_5$:Pr, or $LaF_3$:Nd, for example.

Figure 4:
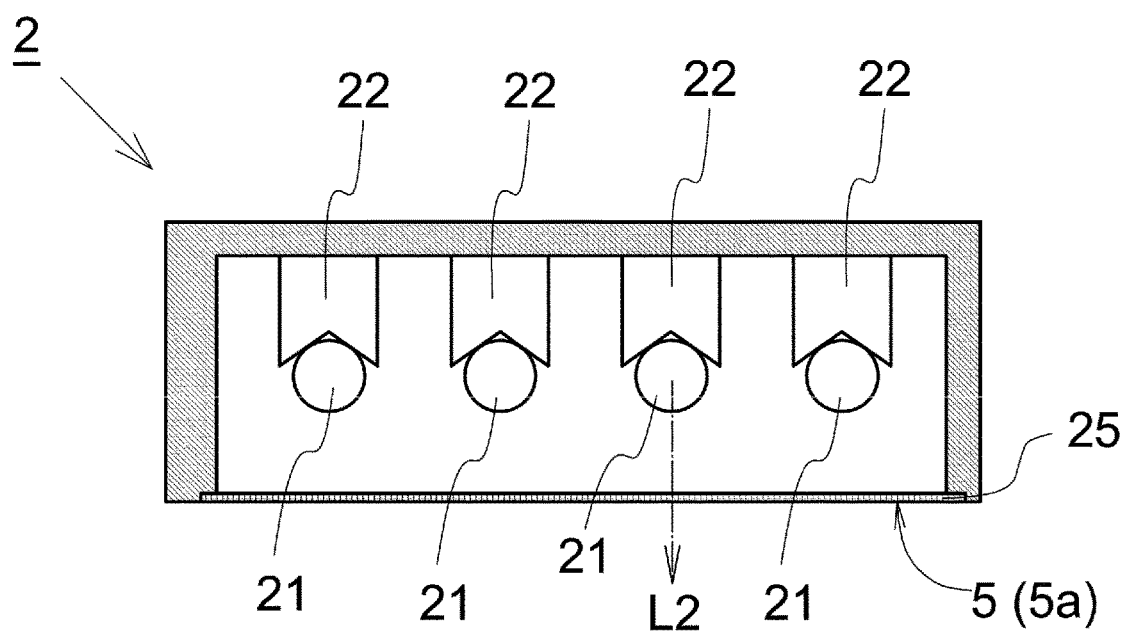
FIG. 4 is a schematic plan view of a UVC light source, viewed in a tube-axis direction of a light-emitting tube.

The UVC light source 2 may include a plurality of excimer lamps. FIG. 4 is a schematic plan view of the UVC light source 2 in which a plurality of excimer lamps are arranged in a predetermined direction, viewed in the tube-axis direction of the light-emitting tube 21 of the excimer lamps. In FIG. 4, only first electrodes 22 that are in contact with outer surfaces of the light-emitting tubes 21 are visible. This is for convenience of illustration, and in practice the presence of second electrodes 22 in a depth direction of a paper surface of the figure may be assumed.

The ultraviolet light L2 emitted from the UVC light source 2 is extracted outside of the lighting device 1 from the area 5a of the light extraction surface 5. If the UVC light source 2 is a KrCl excimer lamp or a KrBr excimer lamp, as in the example described above, the ultraviolet light L2 has a peak wavelength in a range from 200 nm to 230 nm and hardly displays light intensity in a wavelength range of more than 240 nm. However, there are cases where the ultraviolet light L2 displays a very low light intensity even in a wavelength range of more than 240 nm. Hence, as shown in FIG. 4, the light source may include a filter member 25 at least on the area 5a of the light extraction surface 5 (the area through which the ultraviolet light L2 is extracted) to block ultraviolet light in a wavelength range (e.g., 240 nm to 280 nm) that possibly causes an effect on the human body. It is preferable to include the filter member 25 especially when the UVC light source 2 is implemented with a fluorescent material applied to the tube wall of the light-emitting tube 21.

The filter member 25 may also be designed to block the ultraviolet light L2 having a wavelength of less than 200 nm. This suppresses the emission of the ultraviolet light L2 in this wavelength band to the target space and thereby prevents the generation of ozone in the target space. If the UVC light source 2 does not include the filter member that blocks the ultraviolet light L2 having a wavelength of less than 200 nm, the light intensity of the ultraviolet light L2 may have a predetermined upper limit value to keep the amount of ozone incidentally generated in the target space at an extremely low level.

Regarding the excimer lamp shown in FIGS. 3 to 4, as a numerical example, a tube diameter of the light-emitting tube 21 is φ6 mm, a length of the light-emitting tubes 21 is 70 mm, a distance at which the excimer lamps are separated from each other is 14 mm, and a rated power of the excimer lamp is 12 W.

Figure 5:
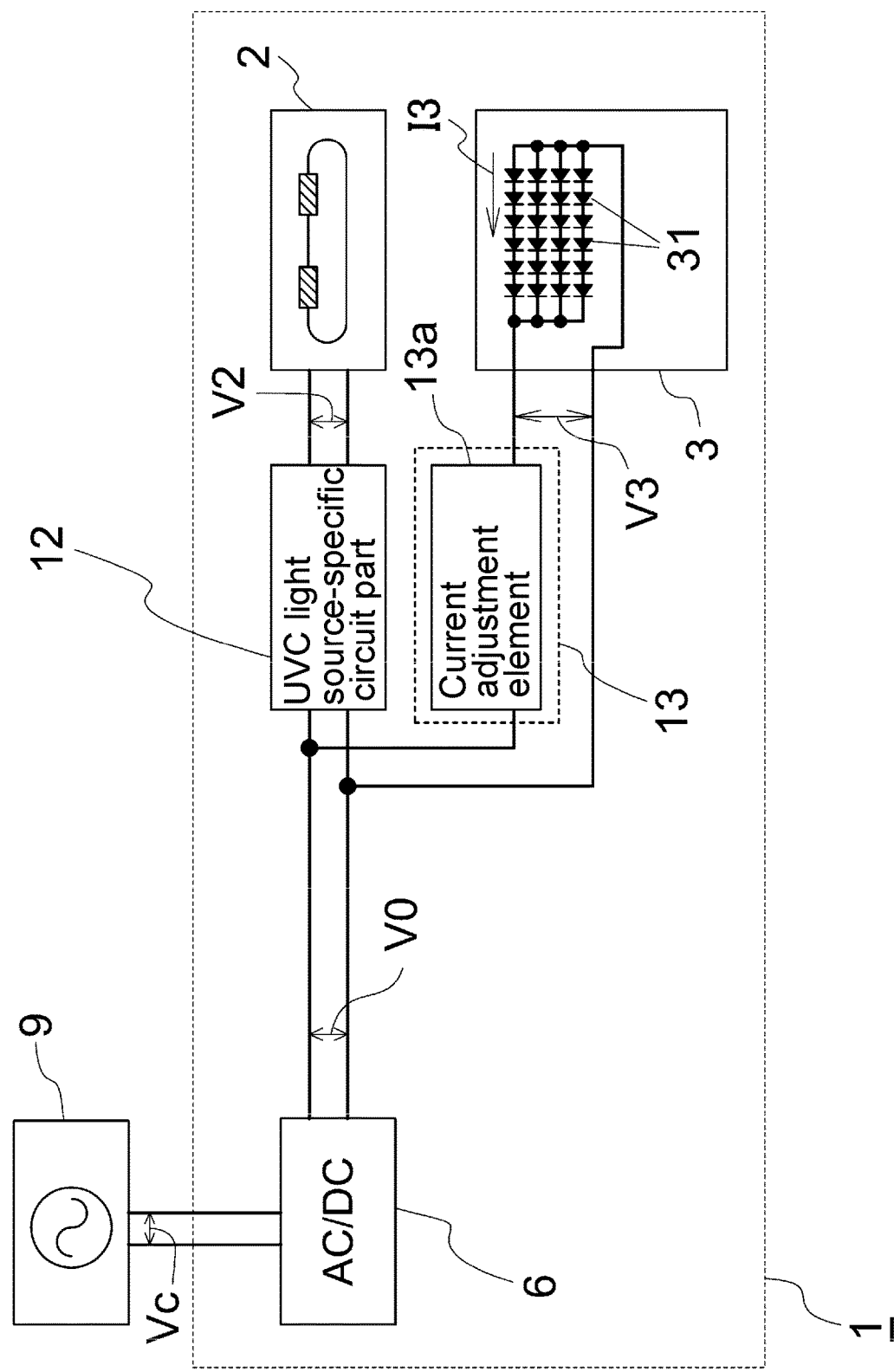
FIG. 5 is a schematic circuit block diagram illustrating a configuration of a lighting circuit included in the lighting device with the inactivation function.

In the present embodiment, the LED light source 3 includes a substrate 30 and a plurality of LED elements 31 mounted on the substrate 30. A plurality of the LED elements 31 are connected in series, and in response to maximum brightness desired for the LED light source 3, a plurality of lines of the series-connected LED elements 31 are connected in parallel. An example shown in FIG. 5 schematically illustrates a case in which six pieces of the LED elements 31 are connected in series and this series-connected circuit (an LED element group) forms four lines that are connected in parallel. In one example, the LED light source 3 can include a device to emit light in a blue area (for example, a wavelength of 450 nm) and a fluorescent material that receives this light to emit fluorescence in a yellow area and combine the two colors to generate the visible light L3 of white color. However, the LED light source should not be limited to this configuration.

FIG. 5 is a schematic circuit block diagram illustrating a configuration of a lighting circuit included in the lighting device 1 of the present embodiment. As described above, the lighting device 1 includes the AC/DC converter 6, the UVC light source-specific circuit part 12, and the LED light source-specific circuit part 13.

Figure 6:
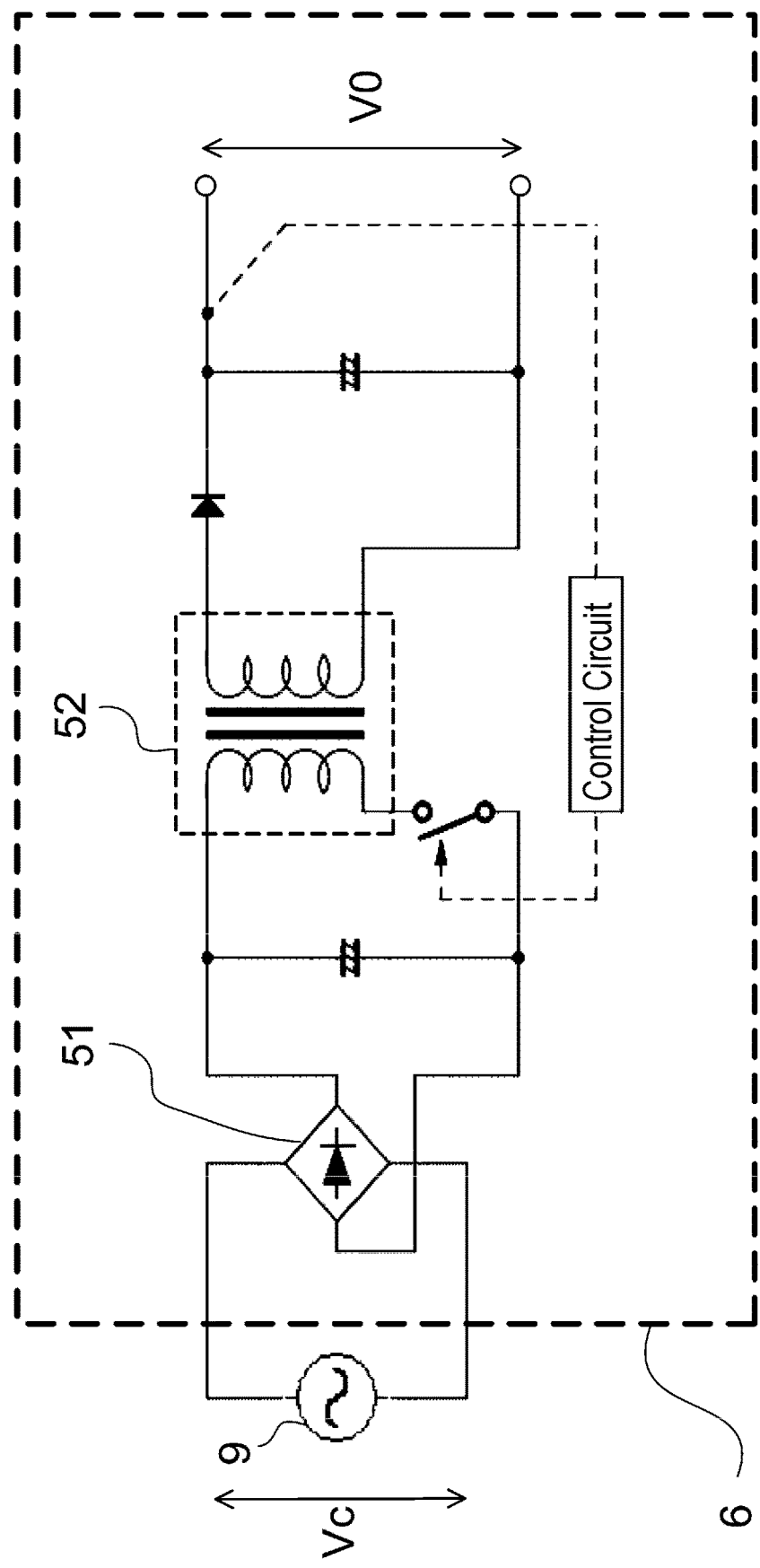
FIG. 6 is an example of a circuit configuration of an AC/DC converter.

The AC/DC converter 6 is a circuit that converts a commercial AC voltage Vc supplied from a commercial power source 9 (corresponding to an "external power source") into a DC voltage V0. An example of a circuit configuration of the AC/DC converter 6 is illustrated in FIG. 6. As shown in FIG. 6, the AC/DC converter 6 includes at least a rectifier circuit 51 and a transformer circuit 52. The rectifier circuit 51 and the transformer circuit 52 each include a large number of elements, and thus the AC/DC converter 6 is a circuit that is relatively prone to increase in size. Although the rectifier circuit 51 is illustrated in a schematic block diagram in FIG. 6, four diode elements are indispensable for a general full-wave rectifier circuit.

In the lighting device 1 of the present embodiment, as shown in FIG. 5, the UVC light source 2 and the LED light source 3 share the AC/DC converter 6. In other words, even though the lighting device 1 includes the UVC light source 2 emitting the ultraviolet light L2 and the LED light source 3 emitting the visible light L3, the AC/DC converter 6 is a single unit, contributing to a reduction in device size.

Figure 7:
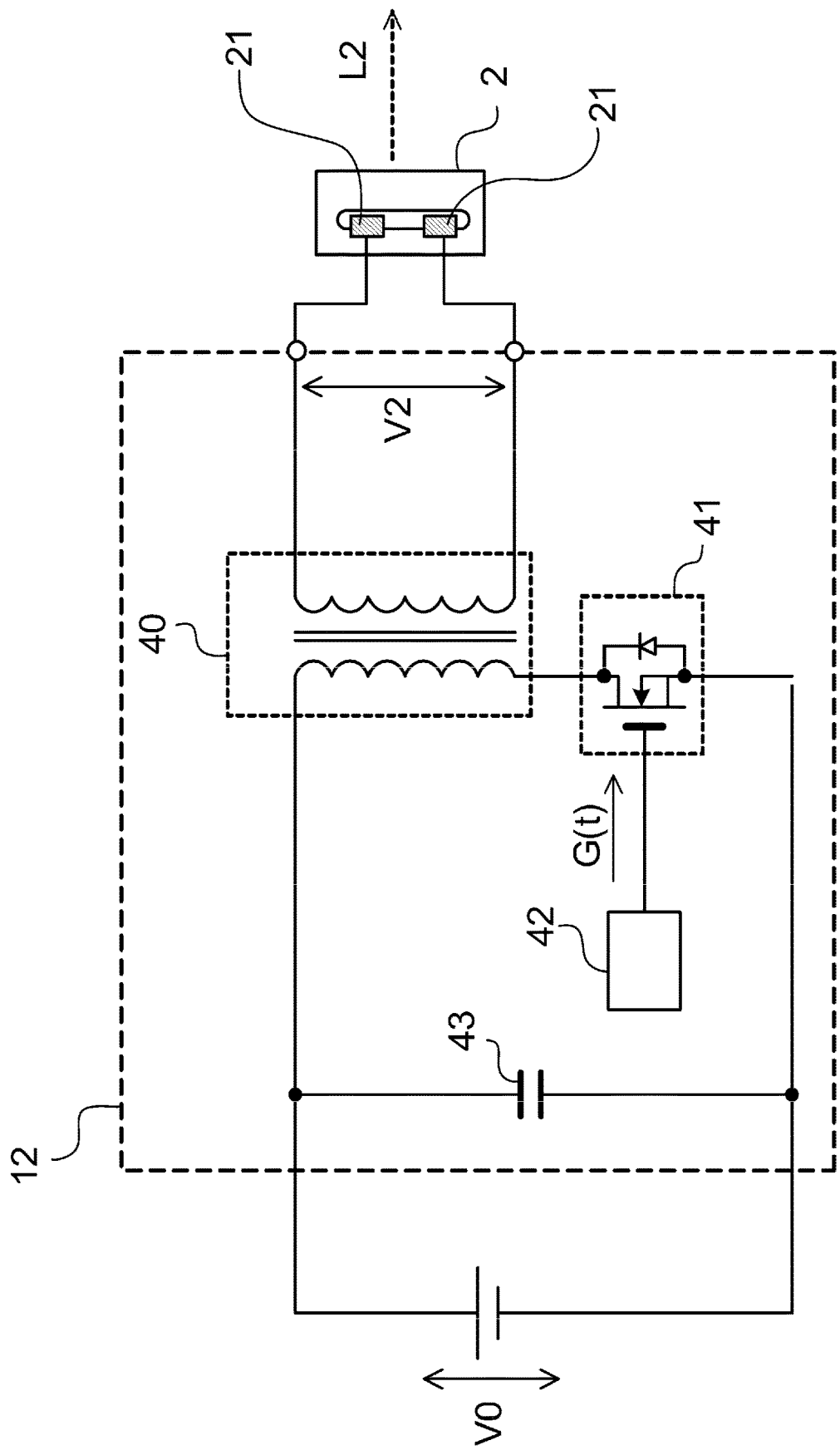
FIG. 7 is an example of a circuit configuration of a UVC light source-specific circuit part.

The UVC light source-specific circuit part 12 is a circuit designed to convert the DC voltage V0 generated by the AC/DC converter 6 into the voltage V2 for lighting the UVC light source 2. An example of a circuit configuration of the UVC light source-specific circuit part 12 is illustrated in FIG. 7. FIG. 7 illustrates a lighting circuit that is commonly referred to as a flyback type and that includes a switching element 41, a controller 42 to perform open/close control of the switching element 41, a smoothing capacitor 43, and a transformer 40. The voltage V2 induced on a secondary side of the transformer 40 is applied between the pair of electrodes (22,22) included in the excimer lamp that makes up the UVC light source 2.

A primary winding of the transformer 40 is connected to the DC voltage V0 through the switching element 41. In the present embodiment, the DC voltage V0 corresponds to an output voltage of the AC/DC converter 6. When the switching element 41 switches to an ON state, a primary current flows from the DC voltage V0 to the primary winding of the transformer 40. The switching element 41 performs ON/OFF control based on a control signal G(t) from the controller 42. When the control signal G(t) changes from Low to High, the switching element 41 shifts from an OFF state to the ON state so that the primary current of the transformer 40 increases as time passes. After that, when the control signal G(t) changes from High to Low, the switching element 41 shifts from the ON state to the OFF state. At this time, the back electromotive force is generated in a secondary winding of the transformer 40 so that an impulse-type secondary voltage V2 is generated. This secondary voltage V2 is applied to the inside of the light-emitting tube 21 of the excimer lamp via the pair of electrodes (22, 22) so that the ultraviolet light L2 is emitted. Subsequently, the switching element 41 repeats ON/OFF control and the voltage V2 of high frequency is thereby continuously applied to the excimer lamp and the ultraviolet light L2 is continuously emitted. Since excimer lamps do not include mercury, adopting an excimer lamp for the UVC light source 2 is excellent in terms of environmental measure.

In the example of FIG. 5, the LED light source 3 is configured by connecting a group of LED elements, formed by six LED elements 31 connected in series, in parallel in four rows. Unless a voltage exceeding a threshold voltage is applied, a current does not flow through the LED element 31 due to a characteristic of the LED element. A level of the flowing current is identified depending on the applied voltage. A rated current that is to flow through the LED element 31 to attain the maximum brightness exists. A voltage generated to both ends of the device in response to a flow of the rated current (herein referred to as a "forward voltage Vf") is determined by a characteristic of the device.

Here, a case in which the LED light source 3 is directly connected to an output terminal of the AC/DC converter 6 is considered. When the DC voltage V0 output from the AC/DC converter 6 (hereinafter sometimes simply referred to as an "output voltage V0 of the AC/DC converter 6") is satisfactorily higher than the product (6·Vf) of the number of the series-connected LED elements 31, i.e. 6, and the forward voltage Vf, it is conceivable that a current exceeding the rated current flows to the LED element group, and each of the LED elements 31 is damaged.

In contrast to this, as shown in FIG. 5, the lighting device 1 of the present embodiment includes a current adjustment element 13a as the LED light source-specific circuit part 13. The current adjustment element 13a may include at least a resistance component. Specifically, on condition that the output voltage of the AC/DC converter 6 is V0, the rated current flowing to the LED element 31 is If, the forward voltage when the rated current If flows to the LED element 31 is Vf, and the number of the LED elements 31 connected in series is n, a resistance component $R_{13}$ included in the current adjustment element 13a is set to a value that substantially agrees with a value of R calculated by the following Formula (1). It should be noted that the term (n·Vf) in Formula (1) corresponds to a voltage applied between both ends of the LED element group made up of a plurality of the series-connected LED elements 31 when the rated current If flows.

The expression "substantially agrees with" means tolerance of an error, and specifically the resistance component $R_{13}$ included in the current adjustment element 13a may be in the range $0.9R \leq R_{13} \leq 1.1R$.

The LED light source-specific circuit part 13 may include a controller for light modulation (not shown) in addition to the current adjustment element 13a. In this case, the current adjustment element 13a is configured to adjust a resistance value based on a signal from the controller. The controller may determine the current I3 that is to flow to the LED element 31 in response to brightness desired for the visible light L3 emitted from the LED light source 3 and adjust the resistance value of the current adjustment element 13a to allow a flow of the current I3 to the LED element 31.

Figure 8:
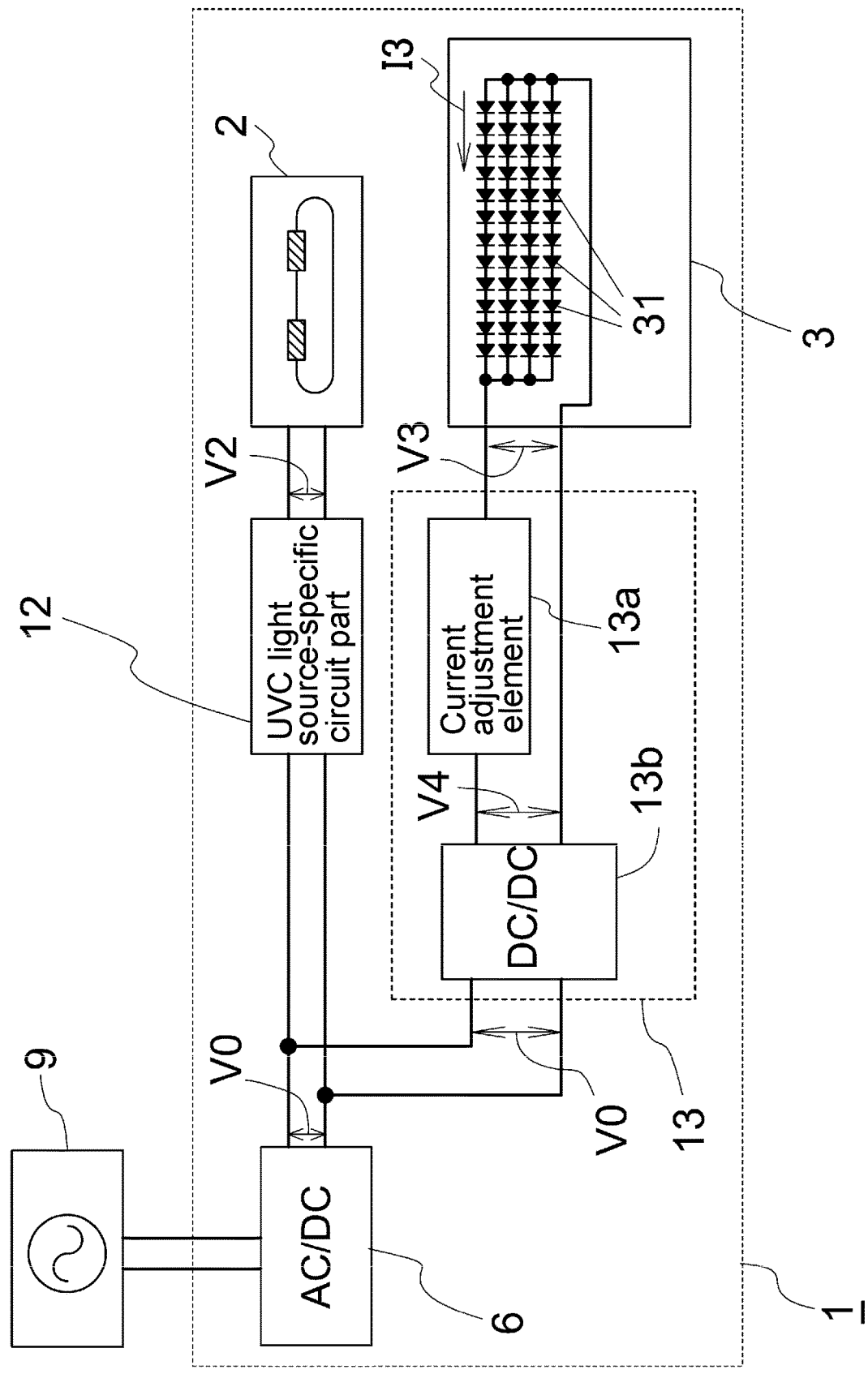
FIG. 8 is a schematic circuit block diagram illustrating another configuration of a lighting circuit included in the lighting device with the inactivation function.

FIG. 8 is a schematic drawing illustrating, in like manner with FIG. 5, an example of another configuration of the lighting device 1. In the example of FIG. 8, the LED light source 3 is configured by connecting a group of LED elements, formed by twelve LED elements 31 connected in series, in parallel in four rows.

When a lighting device 1 with an inactivation function is implemented by adding a new UVC light source 2 to an existing LED lighting device, it is conceivable that the configuration of the LED light source 3 in the existing LED lighting device cannot be readily changed. For instance, when the number of the series-connected LED elements 31 is extremely large as shown in the example of FIG. 8, it is conceivable that the product (n·Vf) of the forward voltage Vf when the rated current If flows to the LED elements 31 and the number of devices n (in this example, 12) is greater than the output voltage V0 of the AC/DC converter 6, in other words, the value (V0−n·Vf) in Formula (1) above is negative.

In such cases, if the LED light source 3 is directly connected to the output terminal of the AC/DC converter 6, a threshold voltage necessary for light emission may not be applied to the LED elements 31 and the LED light source 3 may not emit light.

Figure 9:
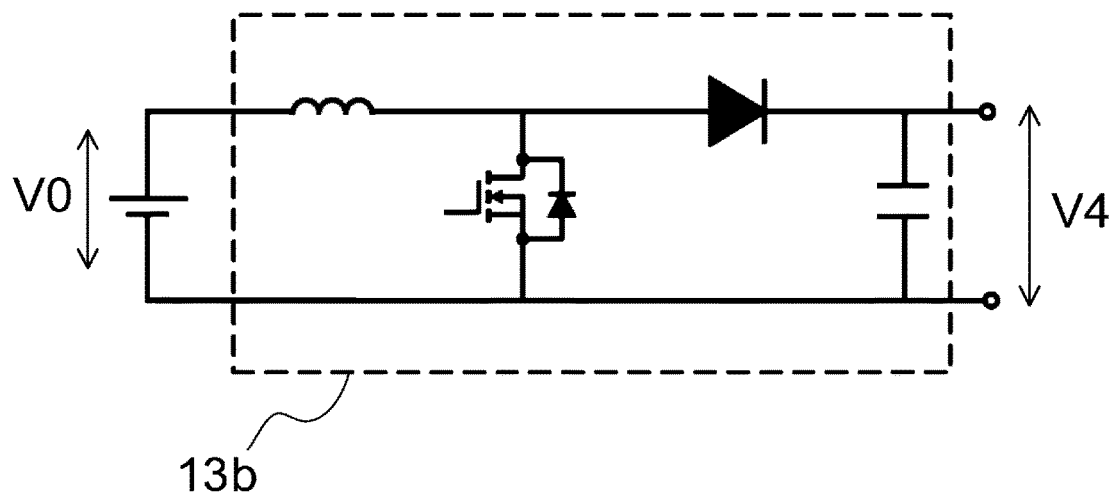
FIG. 9 is an example of a circuit configuration of a DC/DC converter.

In contrast to this, as shown in FIG. 8, the lighting device 1 of the present embodiment includes the current adjustment element 13a and a DC/DC converter 13b as the LED light source-specific circuit part 13. The DC/DC converter 13b is a circuit that increases the output voltage V0 of the AC/DC converter 6 to a DC voltage V4 and is implemented, for example, in a circuit configuration shown in FIG. 9. Unlike the AC/DC converter 6 shown in FIG. 6, the DC/DC converter 13b, as shown in FIG. 9, does not require a rectifier circuit and a transformer and thus can be implemented in small circuit size.

Ideally, the DC/DC converter 13b is designed to increase the output voltage V0 of the AC/DC converter 6 to a DC voltage V4 that is represented by the product (n. Vf) of the forward voltage Vf when the rated current If flows to the LED elements 31 and the number n of the LED elements 31 connected in series.

However, in practice, it is preferable to include the current adjustment element 13a to adjust a flow of the current I3 to the LED elements 31 from the viewpoint of improvement in design flexibility. In this case, the DC/DC converter 13b may increase the output voltage to a DC voltage V4 represented by a voltage higher than (n·Vf), and the current adjustment element 13a may cause the connected resistance component $R_{13}$ to be set to a value that substantially agrees with a value of R calculated by the following Formula (2).

$$R=(V0-n \cdot Vf)/If \qquad (1)$$

$$R=(V4-n \cdot Vf)/If \qquad (2)$$

Other Embodiments

Other embodiments will now be described.

Figure 10:
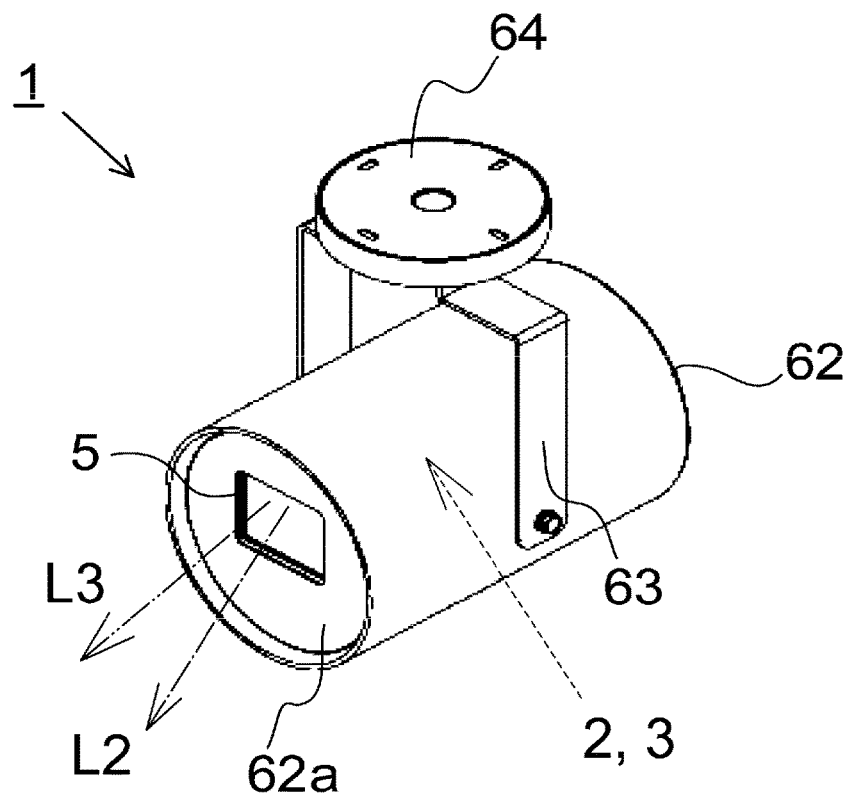
FIG. 10 is a schematic perspective view illustrating a configuration of another embodiment of a lighting device with an inactivation function of the present invention.

<1> The lighting device 1 above is described on the assumption that the lighting device has a downlight-type structure shown in FIG. 1. However, another structure may be used. FIG. 10 is a schematic perspective view of a lighting device 1 of a spotlight type.

A lighting device 1 shown in FIG. 10 includes a lighting fixture 62 that is cylindrical in overall shape, as well as an arm 63 and a holder 64 that is fixed to a ceiling. One end of the arm 63 is attached to a side surface of the lighting fixture 62, and another end of the arm 63 is attached to the holder 64. The lighting fixture 62 constitutes a housing.

Inside the lighting fixture 62, a UVC light source 2, an LED light source 3, and the lighting circuits described above (an AC/DC converter 6, a UVC light source-specific circuit part 12, and an LED light source-specific circuit part 13) are accommodated. A light extraction surface 5 is provided on a front end face 62a of the lighting fixture 62, and ultraviolet light L2 for inactivation and visible light L3 for illumination are emitted from the light extraction surface 5. Regarding the lighting fixture 62, as a numerical example, both the front end face 62a and a rear end face on a side opposite the front end face have a diameter of φ150 mm, and the lighting fixture has a length of 232 mm. The lighting fixture 62 may be designed to rotate or move slantingly in a horizontal or vertical direction to make a direction of emission of the ultraviolet light L2 and the visible light L3 variable.

<2> In the above embodiment, the lighting device is described by exemplifying a case where the UVC light source 2 is an excimer lamp (or a dielectric barrier discharge lamp in which a fluorescent material is disposed on the tube wall of the light-emitting tube 21). However, the present invention can also be applied to a case where the UVC light source 2 is an LED (UV-LED) light source that emits ultraviolet light L2 having a peak wavelength in a wavelength range from 200 nm to 230 nm.

<3> The UVC light source-specific circuit part 12 may include a human sensor. Specifically, when the human sensor detects the presence of a human in the target space, the controller 42 may stop operation control on the switching element 41 to turn off the UVC light source 2. When the absence of any human in the target space for a predetermined period of time or longer is confirmed, the controller 42 may start the operation control on the switching element 41 to light the UVC light source 2.

DESCRIPTION OF REFERENCE SIGNS

1 Lighting device with inactivation function
2 UVC light source
3 LED light source
4 Housing
4a Upper region
4b Lower region
5 Light extraction surface
5a, 5b Light extraction surface area
6 AC/DC converter
9 Commercial power source
10 Substrate
12 UVC light source-specific circuit part
13 LED light source-specific circuit part
13a Current adjustment element
13b DC/DC converter
21 Light-emitting tube
22 Electrode
25 Filter member
30 Substrate
31 LED element
40 Transformer
41 Switching element
42 Controller
43 Smoothing capacitor
51 Rectifier circuit
52 Transformer circuit
62 Lighting fixture
62a Front end face of lighting fixture
63 Arm
64 Holder
G20 Light-emitting gas
L2 Ultraviolet light
L3 Visible light

The invention claimed is:

1. A lighting device with an inactivation function, the lighting device comprising:
   a UVC light source including a lamp to emit ultraviolet light having a peak wavelength in a wavelength range from 200 nm to 230 nm;
   an LED light source to emit visible light;
   a single unit of an AC/DC converter connected to an external power source, the AC/DC converter being configured to convert an AC voltage derived from the external power source into a DC voltage and output the DC voltage;
   a UVC light source-specific circuit part to convert the DC voltage output from the AC/DC converter into a voltage for lighting the UVC light source and supply the voltage to the UVC light source;
   an LED light source-specific circuit part to convert the DC voltage output from the AC/DC converter into a current for lighting the LED light source and supply the current to the LED light source; and
   a housing that accommodates the UVC light source and the LED light source, wherein
   the lighting device with an inactivation function is capable of replacing an existing lighting device where it is installed.

2. The lighting device with an inactivation function according to claim 1, wherein the LED light source includes an LED element group made up of a plurality of LED elements connected in series, either in a single row or in a plurality of rows connected in parallel with each other,
   a voltage applied between both ends of the LED element group is lower than the DC voltage output from the AC/DC converter, and
   the LED light source-specific circuit part includes a resistance component.

3. The lighting device with an inactivation function according to claim 1, wherein the LED light source includes an LED element group made up of a plurality of LED elements connected in series, either in a single row or in a plurality of rows connected in parallel with each other,
   a voltage applied between both ends of the LED element group is higher than the DC voltage output from the AC/DC converter, and
   the LED light source-specific circuit part includes a DC/DC converter to increase the DC voltage output from the AC/DC converter.

4. The lighting device with an inactivation function according to claim 3, wherein the LED light source-specific circuit part includes a resistance component disposed at a place between an output side terminal of the DC/DC converter and the LED light source.

5. The lighting device with an inactivation function according to claim 1, wherein the housing has a shared light extraction surface through which both the ultraviolet light emitted from the UVC light source and the visible light emitted from the LED light source are extracted outside, and the housing forms a shape of a spotlight or a downlight.

6. The lighting device with an inactivation function according to claim 1, wherein the UVC light source includes a filter member to suppress light intensity of a component of the ultraviolet light belonging to a wavelength range of more than 240 nm.

7. The lighting device with an inactivation function according to claim 2, further comprising a housing that accommodates the UVC light source and the LED light source.

8. The lighting device with an inactivation function according to claim 3, further comprising a housing that accommodates the UVC light source and the LED light source.

9. The lighting device with an inactivation function according to claim 4, further comprising a housing that accommodates the UVC light source and the LED light source.

10. The lighting device with an inactivation function according to claim 7, wherein the housing has a shared light extraction surface through which both the ultraviolet light emitted from the UVC light source and the visible light emitted from the LED light source are extracted outside, and the housing forms a shape of a spotlight or a downlight.

11. The lighting device with an inactivation function according to claim 8, wherein the housing has a shared light extraction surface through which both the ultraviolet light emitted from the UVC light source and the visible light emitted from the LED light source are extracted outside, and the housing forms a shape of a spotlight or a downlight.

12. The lighting device with an inactivation function according to claim 9, wherein the housing has a shared light extraction surface through which both the ultraviolet light emitted from the UVC light source and the visible light emitted from the LED light source are extracted outside, and the housing forms a shape of a spotlight or a downlight.

13. The lighting device with an inactivation function according to claim 2, wherein the UVC light source includes a filter member to suppress light intensity of a component of the ultraviolet light belonging to a wavelength range of more than 240 nm.

14. The lighting device with an inactivation function according to claim 3, wherein the UVC light source includes a filter member to suppress light intensity of a component of the ultraviolet light belonging to a wavelength range of more than 240 nm.

15. The lighting device with an inactivation function according to claim 4, wherein the UVC light source includes a filter member to suppress light intensity of a component of the ultraviolet light belonging to a wavelength range of more than 240 nm.

16. The lighting device with an inactivation function according to claim 1, wherein the lamp is a KrCl excimer lamp or a KrBr excimer lamp.

* * * * *